US00PP09423P

United States Patent [19]

VandenBerg

[11] Patent Number: Plant 9,423

[45] Date of Patent: Jan. 9, 1996

[54] CHRYSANTHEMUM PLANT NAMED 'SOFT VOLARE'

[75] Inventor: Cornelis P. VandenBerg, Salinas, Calif.

[73] Assignee: Yoder Brothers, Inc., Barberton, Ohio

[21] Appl. No.: 277,284

[22] Filed: Jul. 21, 1994

[51] Int. Cl.[6] ..... A01H 5/00

[52] U.S. Cl. ..... Plt./82.4

[58] Field of Search ..... Plt./74.1, 82.4

[56] References Cited

U.S. PATENT DOCUMENTS

| | | | |
|---|---|---|---|
| P.P. 8,058 | 12/1992 | VandenBerg | Plt./74.1 |
| P.P. 8,829 | 7/1994 | VandenBerg | Plt./74.1 |
| 4,616,099 | 10/1986 | Sparkes | 47/58 |

OTHER PUBLICATIONS

Chan, 1966, "Chrysanthemum and rose mutations induced by X–rays", Am. Soc. Hort. Sci. Proc., pp. 613–620.

Broertjes, 1966, "Mutation breeding of chrysanthemums", Euphytica, 15:156–162.

Dowrick et al., 1966, "The induction of mutations in Chrysanthemum using X– and gamma radiation", Euphytica, 15:204–210.

Broertjes, et al., 1980, "A mutant of a mutant of a . . . Irradiation of progressive radiation–induced mutants in a mutation breeding programme with *C. morifolium*", Euphytica, 29:526–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods In the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

*Primary Examiner*—Howard J. Locker

*Attorney, Agent, or Firm*—Foley & Lardner

[57] ABSTRACT

A Chrysanthemum plant named Soft Volare particularly characterized by its flat capitulum form; daisy capitulum type; very light pink ray floret color, with the base of the upper side of the ray floret slightly overlaid with light red-purple; diameter across face of capitulum of 76 to 83 mm when fully opened, when grown as a single stem spray cut mum; photoperiodic flowering response to short days when grown in Salinas, Calif., of 50 to 60 days after start of short days; flowering response in Bogota, Colombia of 69 to 71 days; plant height of 71 to 86 cm when grown in Salinas with 11 long days prior to start of short days; height of 99 to 102 cm when grown in Bogota with 14 long days prior to start of short days; peduncle length of the first lateral at flowering after removing the apical bud without growth regulator applications of 8 to 10 cm when grown in Salinas, and 13 to 15 cm when grown in Bogota; peduncle length of the fourth lateral at flowering of 10 to 15 cm when grown in Salinas, and 18 to 20 cm when grown in Bogota; and excellent tolerance to low night temperatures for bud initiation and flower development.

1 Drawing Sheet

The present invention comprises a new and distinct cultivar of Chrysanthemum, botanically known as *Dendranthema grandiflora,* and referred to by the cultivar name Soft Volare.

Soft Volare, identified as 1086 (87-512H13), is a product of a mutation induction program. The new cultivar was discovered and selected by Cornelis P. VandenBerg on Mar. 8, 1991, in a controlled environment in Salinas, Calif. Unrooted cuttings from stock plants of the parent cultivar were exposed to an X-ray source of 2000 rads in Fort Myers, Fla., on Jun. 14, 1990. The irradiated cuttings were grown as stock plants, after which cuttings were taken from these stock plants and subsequently exposed to an X-ray source of 1750 rads in Fort Myers, Fla., on Sep. 30, 1990. The new cultivar was selected from the latter group.

The irradiated parent cultivar was Volare, disclosed in U.S. Plant Pat. No. 8,058, and described as a spray cut mum with a flat capitulum form; daisy capitulum type; light purple ray floret color; diameter across face of capitulum of 80 to 83 mm when fully opened; flowering response period of 49 to 53 days after start of short days in Salinas, Calif., and of 63 to 72 days in Bogota, Colombia; plant height of 74 to 99 cm when grown in Salinas with 3 to 14 long days prior to start of short days, and of 99 to 114 cm when grown in Bogota with 14 to 21 long days prior to start of short days; and excellent tolerance to low night temperatures for bud initiation and flower development. The discription of Volare has a wider range of measurements than the description of Volare in the patent noted. This is based on the continued flowering trials of Volare after filing the plant patent application for Volare.

The irradiation program resulting in Soft Volare had as its primary objective the expansion of color ranges of the parent cultivar Volare. The irradiation program comprised first irradiating cuttings of the parent cultivar at irradiation levels of 2000, 1750 and 1500 rads. These irradiated cuttings were grown out as stock plants, and cuttings were taken from these stock plants and were exposed to an X-ray source of 1750 rads on Sep. 30, 1990. These cuttings were then grown out, and from a total of 225 irradiated plants, a total of 1192 cuttings were harvested, and the cuttings were planted on Jan. 7, 1991. Of these, 17 initial selections were made, which selections were then revegetated and reflowered. Three consecutive flowerings resulted in discarding 12 of the original 17 selections on Dec. 3, 1991. Five codes were retained as Possible Introduction (PI) status. The five retained codes were further tested in Salinas, Calif., and in Bogota, Colombia, ultimately resulting in the decision to discard four selections on Oct. 26, 1992 and Apr. 29, 1993, and the decision to introduce the one remaining selection as Soft Volare.

The first act of asexual reproduction of Soft Volare was accomplished when vegetative cuttings were taken from the original selection in May 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Soft Volare are firmly fixed and are retained through successive generations of asexual reproduction.

Soft Volare has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Colombia, under greenhouse conditions which approximate those generally used in commercial greenhouse practice. The low night temperature tolerance was determined in repeated flowerings in Bogota, Colombia, where average minimum low night temperatures range as low as 6°–9° Celsius.

The following traits have been repeatedly observed and are determined to be basic characteristics of Soft Volare, which, in combination, distinguish this Chrysanthemum as a new and distinct cultivar:

1. Flat capitulum form.
2. Daisy capitulum type.
3. Very light pink ray floret color, with the base of the upper side of the ray florets being slightly overlaid with light red-purple.
4. Diameter across face of capitulum of 76 to 83 mm when fully opened, when grown as a single stem spray cut mum.
5. Photoperiodic flowering response to short days when grown in Salinas, Calif., is 50 to 60 days after start of short days. Flowering response in Bogota, Colombia is 69 to 71 days.
6. Plant height is 71 to 86 cm when grown in Salinas with 11 long days prior to start of short days; height is 99 to 102 cm when grown in Bogota with 14 long days prior to start of short days.
7. Peduncle length of the first lateral at flowering after removing the apical bud without growth regulator applications is 8 to 10 cm when grown in Salinas, and 13 to 15 cm when grown in Bogota. Peduncle length of the fourth lateral at flowering is 10 to 15 cm when grown in Salinas, and 18 to 20 cm when grown in Bogota.
8. Excellent tolerance to low night temperatures for bud initiation and flower development.

The accompanying photographic drawings is a side view of a single stem cut spray mum of Soft Volare, with the colors being as nearly true as possible with illustrations of this type.

Of the commercial cultivars known to the inventor, the most similar in comparison to Soft Volare is the parent cultivar Volare. All traits of Soft Volare are similar to those of Volare, except for the ray floret color and the plant height. The ray floret color of Soft Volare is significantly lighter in color than the ray floret color of Volare. In several flowering trials the plant height of Soft Volare was 2 to 3 cm shorter than the plant height of Volare.

In the following description, color references are made to the Royal Horticultural Society Colour Chart. The color values were determined on plant material grown as a single stem spray cut mum in Salinas, Calif. on Dec. 16, 1993.

Classification:

*Botanical.*—*Dendranthema grandiflora* cv Soft Volare.
*Commercial.*—Flat daisy cut spray mum.

INFLORESCENCE

A. Capitulum:
- *Form.*—Flat.
- *Type.*—Daisy.
- *Diameter across face.*—76 to 83 mm when fully opened.

B. Corolla of ray florets:
- *Color (general tonality from a distance of three meters).*—Very light pink.
- *Color (upper surface).*—56D, with the base of the florets being overlaid with 65B-C.
- *Color (under surface).*—56D.
- *Shape.*—Straight, slightly ribbed.

C. Corolla of disc florets:
- *Color (mature).*—14B.
- *Color (immature).*—144B.

D. Reproductive organs:
- *Androecium.*—Present on disc florets only; moderate pollen.
- *Gynoecium.*—Present on both ray and disc florets.

PLANT

A. General appearance:
- *Height.*—71 to 86 cm when grown in Salinas with 11 long days prior to start of short days; height is 99 to 102 cm when grown in Bogota with 14 long days prior to start of short days.

B. Foliage:
- *Color (upper surface).*—147A.
- *Color (under surface).*—147B.

I claim:

1. A new and distinct Chrysanthemum plant named Soft Volare, as described and illustrated.

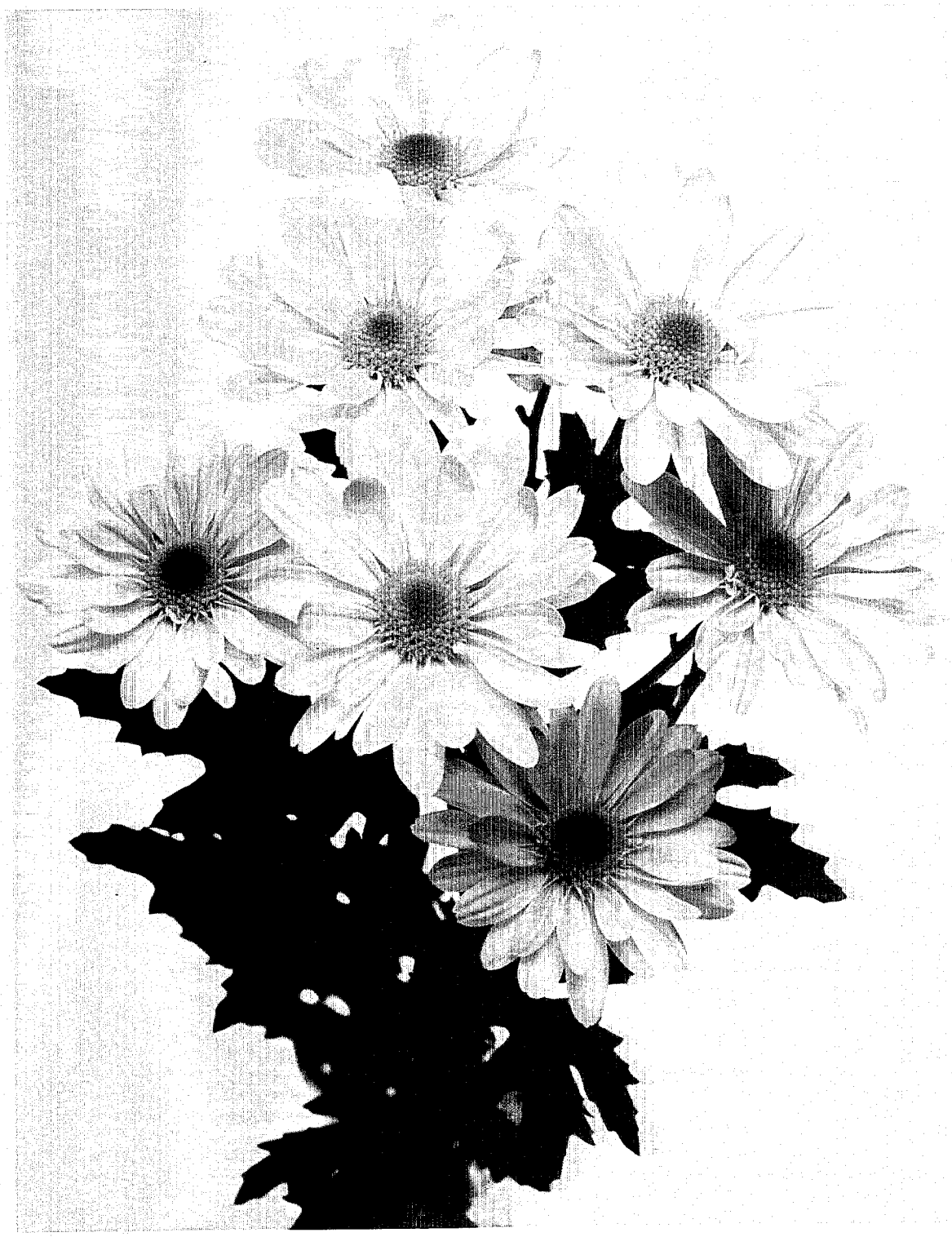

* * * * *